US00PP24215P2

(12) United States Plant Patent
Jacobs

(10) Patent No.: US PP24,215 P2
(45) Date of Patent: Feb. 4, 2014

(54) ***ALSTROEMERIA* PLANT NAMED 'ZALSAFRUZ'**

(50) Latin Name: *Alstroemeria hybrida*
Varietal Denomination: Zalsafruz

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 62 days.

(21) Appl. No.: 13/506,953

(22) Filed: May 25, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Annette Para
(74) *Attorney, Agent, or Firm* — C. A. Whealy

(57) ABSTRACT

A new and distinct cultivar of *Alstroemeria* plant named 'Zalsafruz', characterized by its erect and strong flowering stems; vigorous growth habit; dark red-colored flowers; and excellent postproduction longevity.

1 Drawing Sheet

Botanical designation: *Alstroemeria hybrida.*
Cultivar denomination: 'ZALSAFRUZ'.

BACKGROUND OF THE INVENTION

The present invention relates to a new and distinct cultivar of *Alstroemeria* plant, botanically known as *Alstroemeria hybrida,* commercially used as a cut flower *Alstroemeria*, and hereinafter referred to by the name 'Zalsafruz'.

The new *Alstroemeria* plant is a product of a planned breeding program conducted by the Inventor in Rijsenhout, The Netherlands. The objective of the breeding program is to create new cut flower *Alstroemeria* plants with desirable flower and plant qualities, attractive and unique flower coloration and excellent postproduction longevity.

The new *Alstroemeria* plant originated from a cross-pollination made by the Inventor in Rijsenhout, The Netherlands in June, 2006 of a proprietary *Alstroemeria hybrida* selection identified as code number 2Z110-8, not patented, as the female, or seed, parent with a proprietary *Alstroemeria hybrida* selection identified as code number 42713-2, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in August, 2007.

Asexual reproduction of the new *Alstroemeria* plant by rhizome divisions in a controlled greenhouse environment in Rijsenhout, The Netherlands since September, 2007 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Zalsafruz'.

These characteristics in combination distinguish 'Zalsafruz' as a new and distinct *Alstroemeria* plant:

1. Erect and strong flowering stems.
2. Vigorous growth habit.
3. Dark red-colored flowers.
4. Excellent postproduction longevity.

Plants of the new *Alstroemeria* can be compared to plants of the female parent selection. Plants of the new *Alstroemeria* differ from plants of the female parent selection primarily in flower color as plants of the female parent selection have lighter red-colored flowers.

Plants of the new *Alstroemeria* can be compared to plants of the male parent selection. Plants of the new *Alstroemeria* differ from plants of the male parent selection primarily in inner perianth lateral segment color as plants of the new *Alstroemeria* have dark red and pale yellow-colored inner perianth lateral segments whereas plants of the male parent selection have dark red and white-colored inner perianth lateral segments.

Plants of the new *Alstroemeria* can be compared to plants of *Alstroemeria hybrida* 'Zalsachic', disclosed in U.S. Plant Pat. No. 20,697. In side-by-side comparisons conducted in Rijsenhout, The Netherlands, plants of the new *Alstroemeria* differed primarily from plants of 'Zalsachic' in the following characteristics:

1. Plants of the new *Alstroemeria* had shorter lateral branches than plants of 'Zalsachic'.
2. Plants of the new *Alstroemeria* had smaller inflorescences than plants of 'Zalsachic'.
3. Plants of the new *Alstroemeria* had darker-colored flowers than plants of 'Zalsachic'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant.

The photograph comprises a close-up view of a typical flowering stem of 'Zalsafruz'.

DETAILED BOTANICAL DESCRIPTION

The aforementioned photograph and following observations and measurements describe plants of the new *Alstroemeria* grown during the late summer and early autumn in ground beds in a glass-covered greenhouse in Rijsenhout, The Netherlands. During the production of the plants, day temperatures ranged from 15° C. to 25° C., night temperatures ranged from 10° C. to 15° C., soil temperatures averaged 15° C. and light levels averaged 5,000 lux. Plants were one year old when the photograph and description were taken. In the following description, color references are made to The Royal Horticultural Society Colour Chart, 2007 Edition, except where general terms of ordinary dictionary significance are used.

Botanical classification: *Alstroemeria hybrida* 'Zalsafruz'.

Parentage:

*Female, or seed, parent.*—Proprietary *Alstroemeria hybrida* selection identified as code number 2Z110-8, not patented.

*Male, or pollen, parent.*—Proprietary *Alstroemeria hybrida* selection identified as code number 42713-2, not patented.

Propagation:

*Type.*—In vitro rhizogenesis.

*Time to produce a rooted young plant, summer.*—About 40 days at 16° C. to 25° C.

*Time to produce a rooted young plant, winter.*—About 60 days at 16° C. to 20° C.

*Root description.*—Fibrous, fleshy, thick; color, close to 155D.

*Rooting habit.*—Freely branching; medium density.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright; freely branching, bushy appearance; vigorous growth habit.

*Plant height.*—About 104 cm to 155 cm.

*Plant diameter (spread).*—About 25 cm to 30 cm.

Flowering stem description:

*Aspect.*—Erect.

*Length.*—About 95 cm to 140 cm.

*Diameter.*—About 6 mm to 9 mm.

*Internode length.*—About 0.5 cm to 11 cm.

*Strength.*—Strong.

*Texture.*—Smooth, glabrous.

*Color.*—Close to 144A.

Foliage description:

*Appearance.*—Leaves asymmetrical, simple; sessile.

*Length.*—About 18.5 cm to 25 cm.

*Width.*—About 2.5 cm to 4 cm.

*Shape.*—Elliptic.

*Apex.*—Acute.

*Base.*—Cuneate.

*Margin.*—Entire; weakly undulate.

*Texture, upper and lower surfaces.*—Smooth, glabrous.

*Venation pattern.*—Parallel.

*Color.*—Developing and fully developed leaves, upper surface: Close to 147A; venation, close to 144C. Developing and fully developed leaves, lower surface: Close to 147B; venation, close to 144A.

Flower description:

*Flower type and habit.*—Single cup-shaped flowers arranged in compound umbels; flowers face mostly outwardly; perianth segments separate; freely flowering habit, about five to eight open flowers per flowering stem.

*Natural flowering season.*—Flowering continuous during the spring in The Netherlands; plants begin flowering about 80 to 90 days after planting.

*Fragrance.*—None detected.

*Flower longevity on the plant.*—About four weeks; flowers not persistent.

*Flower longevity as a cut flower.*—About 12 to 16 days; flowers not persistent.

*Flower buds (showing color).*—Length: About 4.5 cm to 5 cm. Diameter: About 1.5 cm to 1.7 cm. Shape: Roughly ovoid. Color: Close to 147A.

*Umbel height.*—About 9.5 cm to 15 cm.

*Umbel diameter.*—About 14.5 cm to 17 cm.

*Flower diameter.*—About 5 cm by 6 cm.

*Flower depth.*—About 5.5 cm to 6.5 cm.

*Perianth.*—Arrangement: Six arranged in two whorls, each whorl with two lateral and one median segments. Inner perianth, lateral segments: Length: About 5.7 cm to 6.4 cm. Width: About 1.7 cm to 2 cm. Shape: Elliptic. Apex: Wishbone-shaped. Base: Attenuate. Margin: Entire; weakly undulate. Texture, upper and lower surfaces: Smooth, glabrous. Color, when opening and fully opened, upper surface: Close to 187B; towards the base, close to 8D; at the base, close to 185C; stripes, close to 187A. Color, when opening and fully opened, lower surface: Close to 187B; towards the base, close to 8D; at the base, close to 185C. Inner perianth, median segment: Length: About 5 cm to 5.5 cm. Width: About 1.6 cm to 1.9 cm. Shape: Elliptic. Apex: Wishbone-shaped. Base: Attenuate. Margin: Entire; weakly undulate. Texture, upper and lower surfaces: Smooth, glabrous. Color, when opening and fully opened, upper surface: Close to 187B. Color, when opening and fully opened, lower surface: Close to 187B. Outer perianth, lateral segments: Length: About 5.2 cm to 5.9 cm. Width: About 3 cm to 3.6 cm. Shape: Obovate. Apex: Embedded point. Base: Attenuate. Margin: Entire; weakly undulate. Texture, upper and lower surfaces: Smooth, glabrous. Color, when opening and fully opened, upper surface: Close to 187B. Color, when opening and fully opened, lower surface: Close to 187B. Outer perianth, median segment: Length: About 5.5 cm to 6.3 cm. Width: About 3.1 cm to 3.6 cm. Shape: Obovate. Apex: Embedded point. Base: Attenuate. Margin: Entire; weakly undulate. Texture, upper and lower surfaces: Smooth, glabrous. Color, when opening and fully opened, upper surface: Close to 187B. Color, when opening and fully opened, lower surface: Close to 187B.

*Pedicels.*—Length: About 0.5 cm to 10 cm. Diameter: About 2 mm to 4 mm. Strength: Strong. Angle: About 20° to 30° from vertical. Texture: Smooth, glabrous. Color, upper and lower surfaces: Close to 144A.

*Reproductive organs.*—Stamens: Quantity per flower: Six. Anther shape: Elliptic. Anther length: About 2 mm to 9 mm. Anther color: Close to 187A. Pollen amount: Abundant. Pollen color: Close to N186C. Pistils: Quantity per flower: One. Style length: About 2.5 cm to 3 cm. Style color: Close to 187C. Stigma color: Close to 187C. Ovary color: Close to 146B.

*Seeds and fruits.*—Seed and fruit development has not been observed on plants of the new *Alstroemeria.*

Disease & pest resistance: Plants of the new *Alstroemeria* have not been observed to be resistant to pathogens and pests common to *Alstroemeria* plants.

Temperature tolerance: Plants of the new *Alstroemeria* have been observed to tolerate temperatures from about 0° C. to about 40° C.

It is claimed:

1. A new and distinct *Alstroemeria* plant named 'Zalsafruz' as illustrated and described.

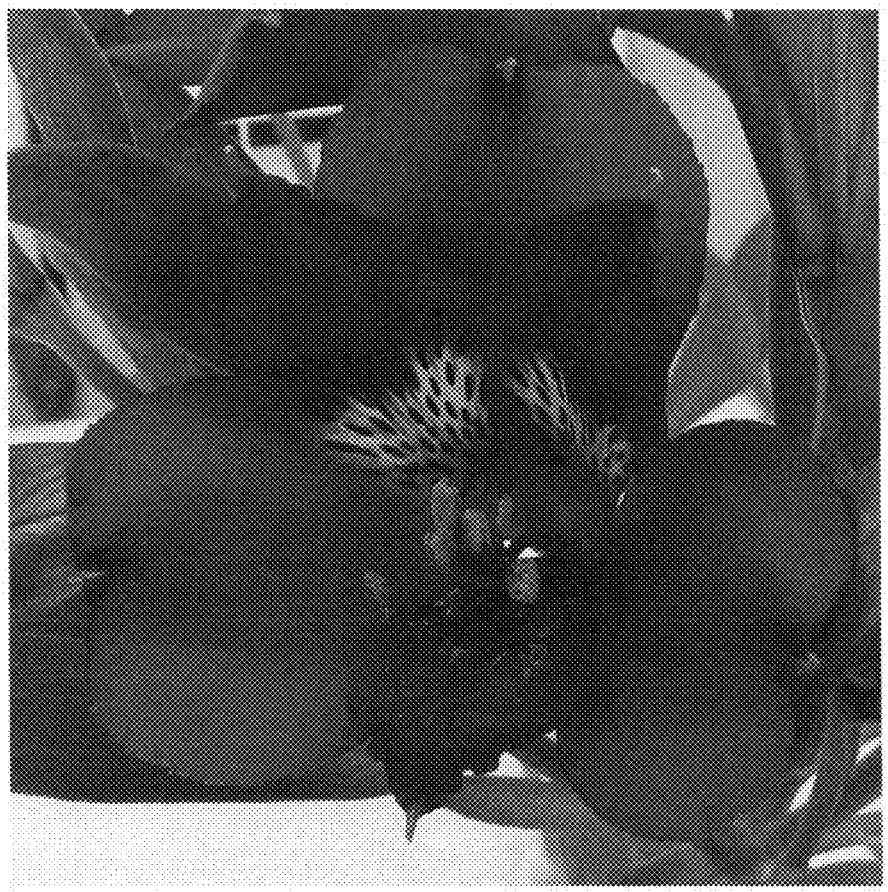

* * * * *